(12) United States Patent
Green et al.

(10) Patent No.: US 7,999,547 B2
(45) Date of Patent: Aug. 16, 2011

(54) SYSTEM FOR MAGNETIC RESONANCE IMAGING ASSISTED SURGERY

(75) Inventors: Charles A. Green, Holbrook, NY (US);
Arto Cinoglu, Oceanside, NY (US);
William H. Wahl, Smithtown, NY (US)

(73) Assignee: Fonar Corporation, Melville, NY (US)

( * ) Notice: Subject to any disclaimer, the term of this patent is extended or adjusted under 35 U.S.C. 154(b) by 64 days.

(21) Appl. No.: 12/381,718

(22) Filed: Mar. 16, 2009

(65) Prior Publication Data

US 2009/0234222 A1 Sep. 17, 2009

Related U.S. Application Data

(62) Division of application No. 11/726,700, filed on Mar. 21, 2007, now Pat. No. 7,525,312.

(60) Provisional application No. 60/784,151, filed on Mar. 21, 2006.

(51) Int. Cl.
*G01V 3/00* (2006.01)
(52) U.S. Cl. .................. 324/318; 324/319; 600/422
(58) Field of Classification Search .................. 324/318, 324/319; 600/422
See application file for complete search history.

(56) References Cited

U.S. PATENT DOCUMENTS

| 5,085,219 | A | | 2/1992 | Ortendahl et al. | |
|---|---|---|---|---|---|
| 5,396,905 | A | | 3/1995 | Newman et al. | |
| 5,483,961 | A | | 1/1996 | Kelly et al. | |
| 5,735,278 | A | * | 4/1998 | Hoult et al. | ............. 600/422 |
| 5,787,886 | A | | 8/1998 | Kelly et al. | |
| 5,808,468 | A | | 9/1998 | Bis et al. | |
| 6,128,522 | A | * | 10/2000 | Acker et al. | ............. 600/411 |
| 6,141,579 | A | | 10/2000 | Bonutti | |
| 6,198,962 | B1 | | 3/2001 | Su | |
| 6,201,394 | B1 | * | 3/2001 | Danby et al. | ............. 324/319 |
| 6,208,145 | B1 | | 3/2001 | Danby et al. | |
| 6,317,619 | B1 | * | 11/2001 | Boernert et al. | ............. 600/410 |
| 6,418,337 | B1 | | 7/2002 | Torchia et al. | |
| 6,784,665 | B1 | | 8/2004 | Chan et al. | |
| 2004/0030241 | A1 | | 2/2004 | Green et al. | |

* cited by examiner

*Primary Examiner* — Louis M Arana
(74) *Attorney, Agent, or Firm* — Lerner, David, Littenberg, Krumholz & Mentlik, LLP

(57) ABSTRACT

A system and method for magnetic resonance imaging assisted surgery. The system includes an antenna support assembly and an antenna that are used to acquire real time images of the surgical site that may be used by a surgeon to more accurately perform the surgical procedure. The method comprises acquiring real time images of the surgical site and feeding back the images to a surgeon performing the surgical procedure.

9 Claims, 12 Drawing Sheets

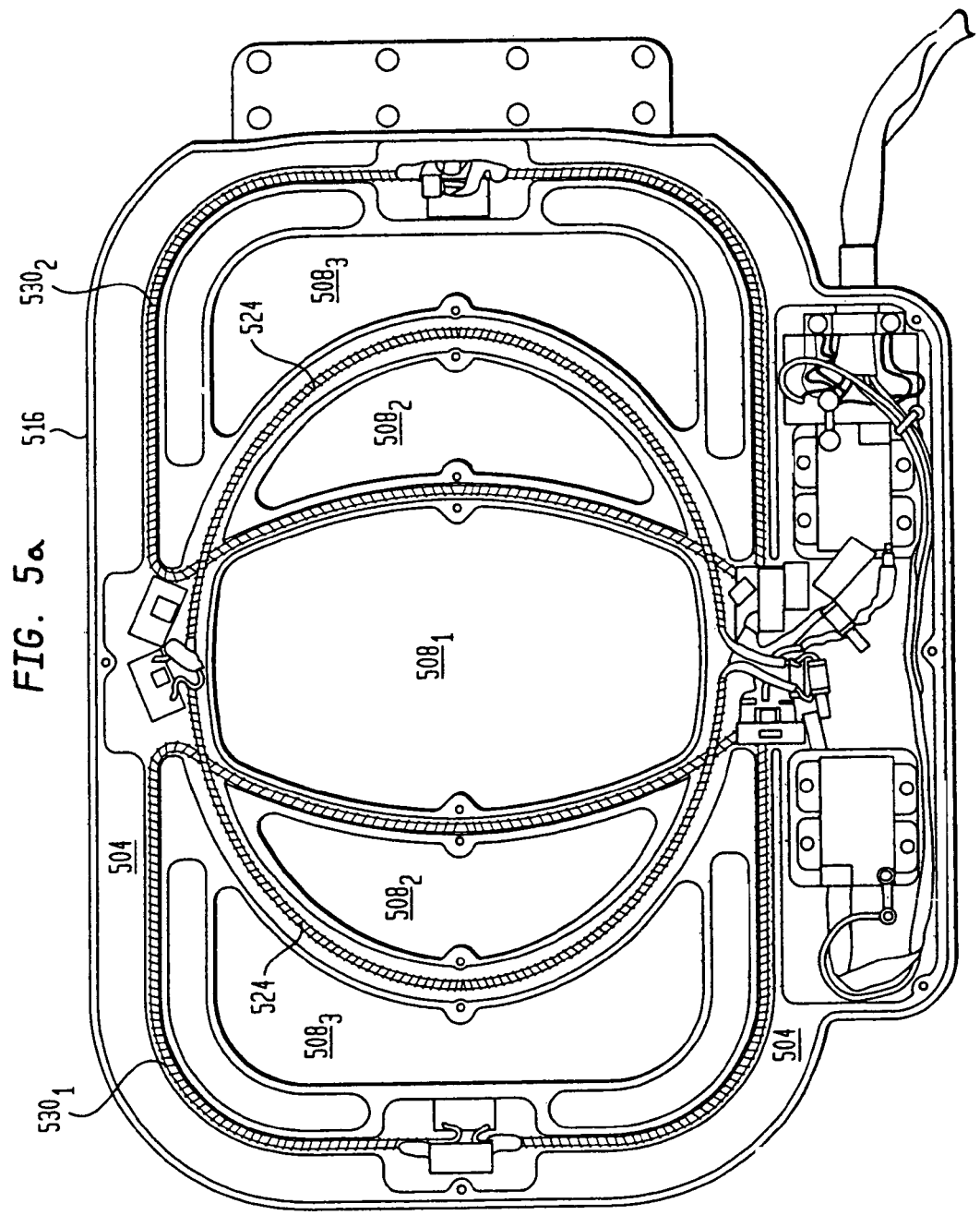

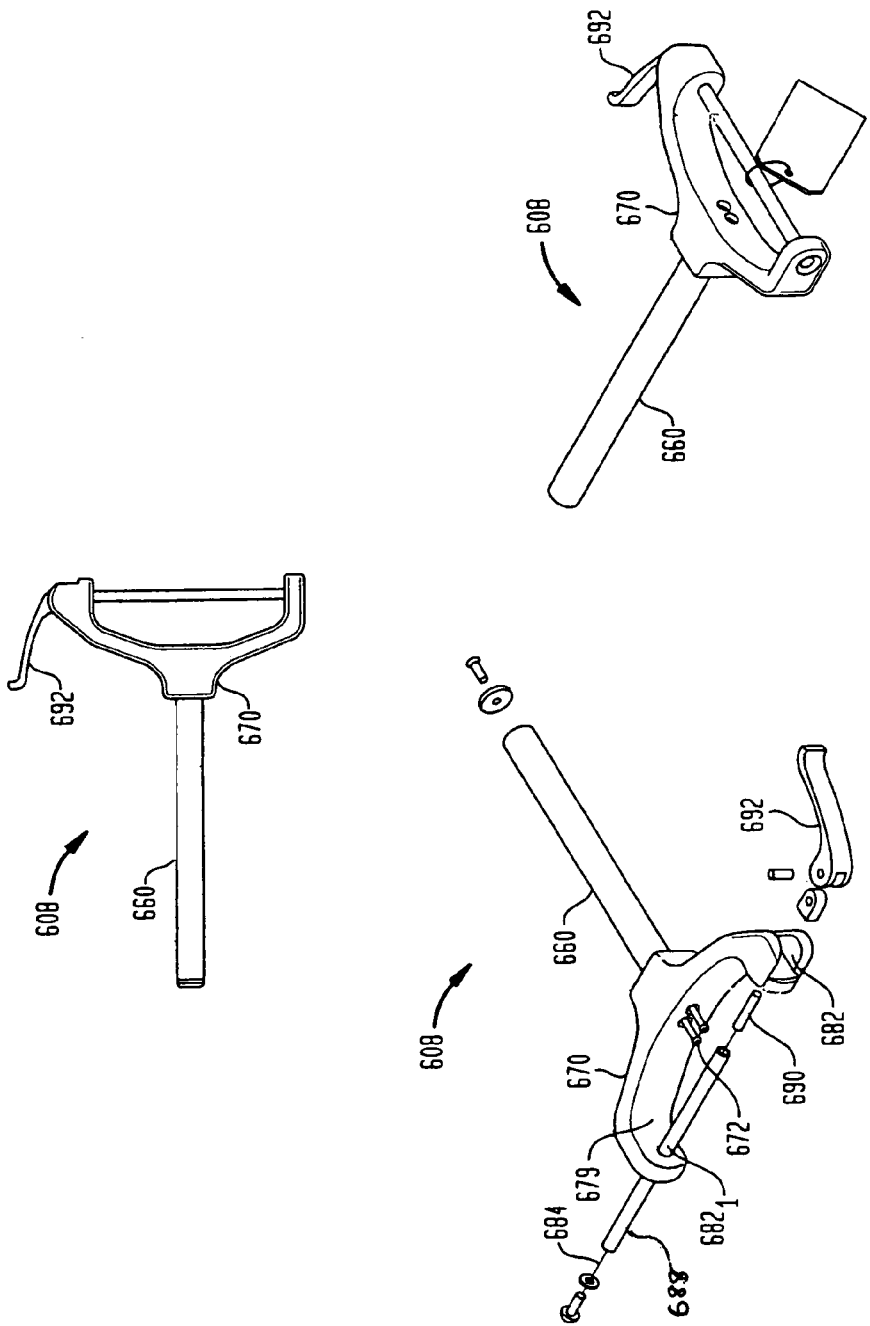

SYSTEM FOR MAGNETIC RESONANCE IMAGING ASSISTED SURGERY

CROSS-REFERENCE TO RELATED APPLICATIONS

This application is a divisional of U.S. application Ser. No. 11/276,700, filed on Mar. 21, 2007, which claims the benefit of the filing date of U.S. Provisional Patent Application No. 60/784,151 filed Mar. 21, 2006, the disclosures of which are hereby incorporated herein by reference.

BACKGROUND OF THE INVENTION

The present patent application relates to magnetic resonance imaging apparatus and methods for using such apparatus in surgical procedures.

In magnetic resonance imaging, an object to be imaged as, for example, a body of a human subject is exposed to a strong, substantially constant static magnetic field. The static magnetic field causes the spin vectors of certain atomic nuclei within the body to randomly rotate or "precess" around an axis parallel to the direction of the static magnetic field. Radio frequency excitation energy is applied to the body, and this energy causes the nuclei to "precess" in phase and in an excited state. As the precessing atomic nuclei relax, weak radio frequency signals are emitted; such radio frequency signals are referred to herein as magnetic resonance signals.

Different tissues produce different signal characteristics. Furthermore, relaxation times are the dominant factor in determining signal strength. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

Many conventional magnetic resonance imaging instruments require that a patient lie on a horizontal bed that is then advanced into a tubular bore within a super-conducting solenoidal magnet used to generate the static magnetic field. These units force the patient to undergo an intensely claustrophobic experience while being imaged. Other forms of magnetic resonance imaging apparatus, commonly referred to as "open MRI apparatus," were developed to provide a less claustrophobic experience to the patient and greater access to the patient by medical personnel during the imaging procedure. However, even in this improved apparatus, the patient was still positioned inside the apparatus, and medical personnel attending to the patient would reach into the apparatus from outside, so that components of the apparatus still obstructed access to some extent.

As described in U.S. Pat. Nos. 6,335,623 and 6,541,973, which are assigned to the assignee of the present application, the disclosures of which are hereby incorporated by reference herein, this problem can be solved completely by providing space within the apparatus itself to accommodate medical personnel in addition to the patient. Thus, as shown in certain embodiments disclosed in the '973 and '623 patents, the magnet may include a ferromagnetic frame incorporating a floor, a ceiling and a pair of side walls extending between the floor and the ceiling, a lower ferromagnetic pole structure projecting upwardly from the floor and an upper ferromagnetic pole structure projecting downwardly from the ceiling. The projecting pole structures define a patient-receiving space between them. The magnet also includes flux generating elements such as resistive or superconducting coils or permanent magnets arranged to direct flux through the frame so that the flux passes through the patient-receiving space between the pole structures and returns through the side walls, floor and ceiling. The space between the side walls may be of essentially any size, but is desirably sufficient so that medical personnel can enter into the space along with the patient. In effect, the frame preferably forms a room with a pole structure projecting down from the ceiling and another pole structure projecting up from the floor. The medical personnel inside the room have essentially unobstructed access to the patient from any side. It is, thus, quite practical to perform surgery or other medical procedure on a patient while the patient is in the patient-receiving space of the MRI apparatus. The room defined by the magnet frame may be equipped with features normally found in operating rooms, so that the magnet effectively becomes an MRI-capable operating room. Thus, surgery or other procedures can be performed under MRI guidance.

As shown in detail in the '973 patent, a patient positioning device may include a chassis having a pair of vertically extending end portions or leg portions and a bridge portion extending between these leg portions. The end portions of the chassis are spaced apart by a distance greater than the dimension of the lower pole structure. A bed is movably mounted to the chassis so that the bed can move and pivot in various directions relative to the chassis. The chassis is provided with wheels so that the patient can be positioned in the patient-receiving space of the magnet by placing the patient on the bed and wheeling the chassis into position, with the end portions of chassis disposed on opposite sides of the lower pole structure and with the bridge portion of the chassis spanning across the lower pole structure, so that the bridge portion of the chassis and the bed lie within the patient-receiving space. The patient can then be repositioned in various ways as by turning the bed about a vertical axis, tilting the bed about a horizontal axis or sliding the bed relative to the chassis. These arrangements provide extraordinary versatility in imaging of the patient and in positioning the patient for medical procedures.

However, further improvement would be desirable. For example, it is desirable to have a magnetic resonance image of the portion of the patient's anatomy on which surgery is being performed. Typically, MRI assisted surgical procedures comprise scanning the patient's anatomy of interest beforehand. The scans are then referred to during surgery or in some instances the scans are used to build models. The models are then used by a surgeon in planning the actual surgery or in a preoperative simulation of the surgery. Additional preoperative uses of these images include localization of the surgical site and blood vessel and anatomical relationships. Although these techniques enhance the surgical procedure, they do not provide a surgeon with a real time view of the surgical site so as to provide direct visual feedback to the surgeon.

The present invention addresses the foregoing needs.

SUMMARY OF THE INVENTION

In one aspect the present invention comprises a system for magnetic resonance imaging assisted surgery. The system preferably comprises a magnet having a lower pole and an upper pole arranged along a vertical axis defining a patient receiving space therebetween; a bed positioned within the patient receiving space for supporting a patient, the bed having a frame and a support surface onto which the patient is positioned; and an antenna support assembly mounted to the bed, the support assembly being adapted to support a housing having one or more antenna coils, the housing comprising a skeletal structure that allows access to the portion of patient's anatomy adjacent the housing and from which signals are received by the coils.

In another aspect, the present invention may comprise a method for performing a surgical procedure. The method preferably comprises positioning a patient on bed in a receiving space of a magnetic resonance imaging magnet; positioning an antenna coil assembly adjacent to a portion of the patient's anatomy; acquiring a magnetic resonance image of the patient's anatomy adjacent the antenna coil assembly; performing a surgical procedure on the patient's anatomy adjacent the antenna coil assembly; and repetitively acquiring images of the patient's anatomy adjacent the antenna coil assembly as the surgical procedure is performed.

BRIEF DESCRIPTION OF THE DRAWINGS

FIG. 5A shows a housing of a planar quad coil assembly with a section of the housing removed to reveal the coil geometry.

FIG. 6C shows several views of a coil locking sub-assembly in accordance with an aspect of the present invention.

DETAILED DESCRIPTION

Figure 1:
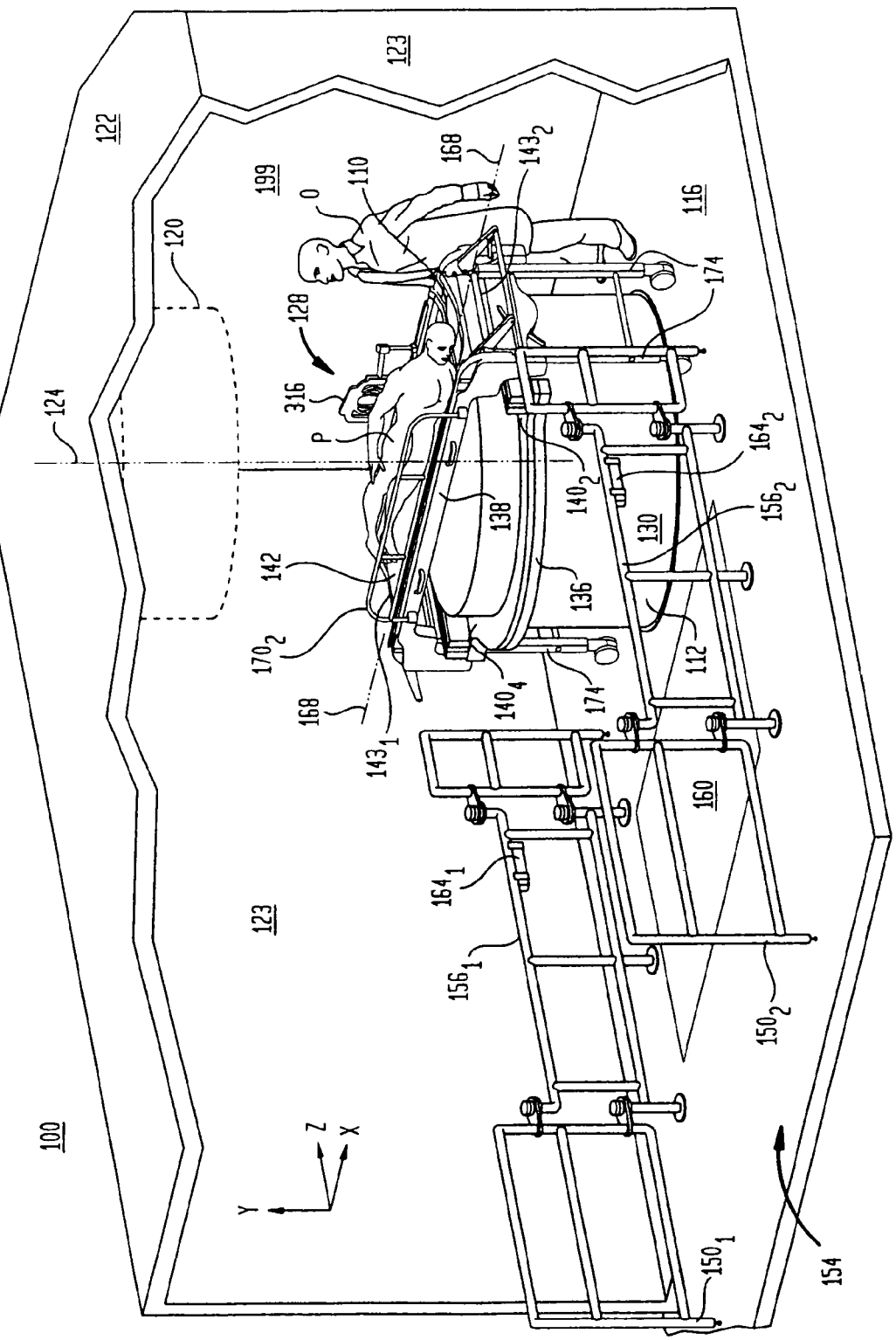
FIG. 1 is a schematic of a magnetic resonance imaging system in accordance with an aspect of the present invention.

Turning now to FIG. 1, there is shown a magnetic resonance imaging system 100 in accordance with an aspect of the present invention. The system 100 includes a magnet (while not shown in full, components of the magnet are shown and identified subsequently) and a patient support apparatus 110. The magnet includes a lower magnet pole structure 112 that projects upwardly from a floor 116. As is discussed in greater detail in U.S. application Ser. No. 11/236,184, the disclosure of which is incorporated herein by reference, the floor 116 is a false floor that is supported above a well floor and is isolated from the magnet. The magnet also includes an upper magnet pole structure 120 that projects downwardly from a ceiling 122. For clarity, the upper magnet pole structure 120 is shown schematically in broken lines projecting downwardly through a portion of the ceiling 122. Other structures associated with the magnet are located beneath floor 116, above the ceiling 122, and behind the side walls 123, but are not shown for clarity. In addition, a front wall (not shown) is also used to house the system in a room, which may serve as an operating theater. The lower and upper pole structures 112, 120 are aligned with each other along a polar axis 124 that generally extends vertically in the y-direction. The upper and lower pole structures 112, 120 are spaced apart so as to define a patient receiving space 128 therebetween. As shown in FIG. 1, a patient P may be positioned within the receiving space 128 using the patient support system 110. Other personnel may then access the patient P while in patient receiving space 128. These personnel may include doctors, nurses, technicians or an entire surgical team. Advantageously, the system 100 is housed in a room that forms an operating theater.

As shown in FIG. 1, the lower pole structure 112 is surrounded by a shroud 130 that is equipped to receive the patient support apparatus 110 that is also included with the system 100. The shroud 130 is equipped with a rotatable frame 136 that includes ledges 140 onto which the patient support apparatus 110 may be docked and mounted. When the patient support apparatus 110 is mounted to the frame 136 it may be rotated about the polar axis 124. In addition, the patient support apparatus 110 includes a frame 138 onto which a bed or slab 142 is slidably mounted such that slab 142 is allowed to cantilever relative to the magnet pole. As such, either end of patient support apparatus 110 may project outward from the magnet pole and be rotated. This allows any portion of the patient's anatomy to be located in the imaging volume and/or iso-center of the magnet, i.e., within the center of the imaging volume.

The system 100 further includes a pair of safety gates 150 that are located at the front 154 of the magnet. Each gate 150 is connected to a rail 156, which is mounted to the floor 116. A lift platform 160 forms part of an elevator system, which is located towards the front 154 of the magnet. The rails 156 are equipped with a light gate sensor system 164 that detects the presence or absence of an object, e.g., medical personnel or bed 142, that may be supported by the platform 160. The light gate system 164 works in conjunction with an elevator system to automatically raise the lift platform 160 under certain conditions. In particular, if the lift platform 160 is recessed beneath the floor 116 and the gates 150 are opened, the lift platform 160 is automatically raised to be level with the floor 116, unless a person or object is in the path of the light gate sensors 164.

As an overview, the system 100 operates as follows. A patient is preferably loaded onto the patient support apparatus 110 in a staging area. The patient is then transported through the front 154 and positioned on the platform 160. While on the platform 160, the patient support apparatus is positioned with its longitudinal axis 168 aligned with the x-axis. The patient support apparatus 110 may then be raised to a suitable height such that it clears the lower magnet pole 112. The patient support apparatus 110 is then moved over the magnet pole 112 into the patient receiving space or gap 128. Once properly positioned over the pole 112, the apparatus 110 is then lowered to engage the rotatable frame 136 at ledges 140. With the patient support apparatus 110 mounted onto the frame 136, safety rails 170 and legs 174 are then removed from the patient support apparatus. The patient may then be rotated and translated as discussed above so that the portion of the patient's anatomy to be scanned is located in the magnet's isocenter.

In addition to performing scanning, the system 100 also provides a versatile and open enough environment that can also accommodate one or more medical personnel O in addition to the patient. For example, the system may be used in performing a biopsy or other medical procedure. In particular, the space around the poles provides an unobstructed view of a patient supported on the bed 142 in the gap 128. An attendant or medical personnel may have 360° access to the patient from all locations. In addition, the platform 160 may be adjusted so as to accommodate the height of a doctor standing on the platform, who may be performing medical procedures using the images provided by a scan to pinpoint the location of tumors, tissue, bones or organs. In that regard, the system may also include a display (not shown) that is attached to the upper magnet pole so that a surgeon could view images in real time. The magnet design therefore provides an environment that can function as an operating room.

As best seen in FIG. 1, in a preferred embodiment, an antenna 316 is attached to the support apparatus 110 along an edge of a frame 138. In addition, the patient is shown as lying on a side such that the antenna can be placed adjacent to a portion of the patient's anatomy. As shown, the antenna is placed next to the patient's posterior surface, although the patient and antenna may be maneuvered so that the antenna is adjacent to other anatomical areas of interest. In accordance with an aspect of the present invention, the antenna comprises a skeletal structure (e.g., see FIGS. 3 and 7) that allows a surgeon access to the patient's anatomy while the antenna receives resonance signals from the anatomical area of interest. This advantageously allows the surgeon, for example, to view real time MR images of the patient's anatomy on a conveniently placed display while conducting a medical procedure. Such procedures may include actual surgery or biopsies. The real time MR images desirably enhance the medical procedure by providing real time views of the surgical site during the procedure.

Alternatively, the system may be used to scan patients on an ambulatory or outpatient basis. In that regard, the system allows two or more patient support apparatus to be located in a staging area and used to load patients. When located in the staging area, the legs and wheels of the patient support apparatus are attached to the frame apparatus. In this mode, the patient apparatus is not docked to the lower pole, but is instead used to support and transport the patient to the front of the room housing the magnet. The patients may then be sequentially routed through the magnet thereby improving the throughput of the system 100.

Figure 2:
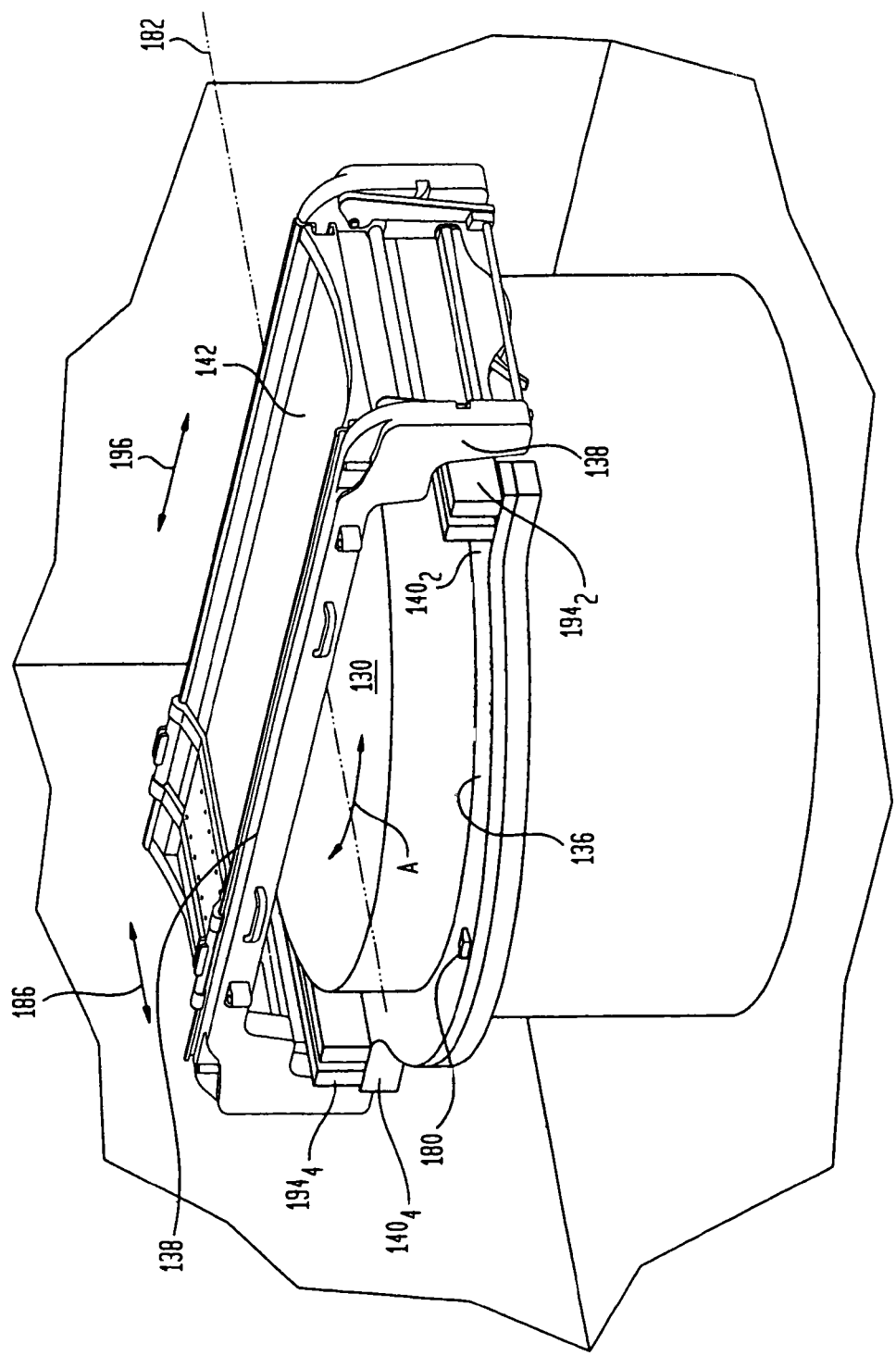
FIG. 2 is a perspective view of a magnetic resonance system in accordance with an aspect of the present invention.

With the bed 142 mounted to the frame 138, the legs 174 (see FIG. 1) may then be preferably removed. In the preferred embodiment, the legs are removed by grasping bar 143 and rotating it downwards 90° and towards the magnet pole. A lever (not shown) is then preferably used to release the legs 174 from the frame 138. FIG. 2 shows the bed 142 after it is mounted to the pole 130 and the legs have been removed. The legs may include sensors that detect the presence of a load on the legs and prevent the legs from being removed from the bed frame.

As illustrated in FIG. 2, once the bed is mounted onto the pole 130, or more particularly to rotation frame 136 at ledge 140, it may then be rotated around the pole as is depicted by arrow A. As an additional safety feature, the rotation frame 136 is equipped with one or more stops 180 that allow the bed 142 to be docked at 0° of rotation as shown in FIG. 2, or 90° of rotation (line 182) on the stop 180 shown. Note, however, that the bed 142 may rotate 180° or 360° about the polar axis. In addition to rotation about the pole 130, the bed 142 may slide side-to-side along direction 186 on beams 194, which preferably telescope along direction 186. The bed 142 may also cantilever on its frame 138 along the direction 196. These additional adjustments allow for greater flexibility with respect to bringing a patient close to a doctor, who is standing at the edge of the pole.

Figure 3:
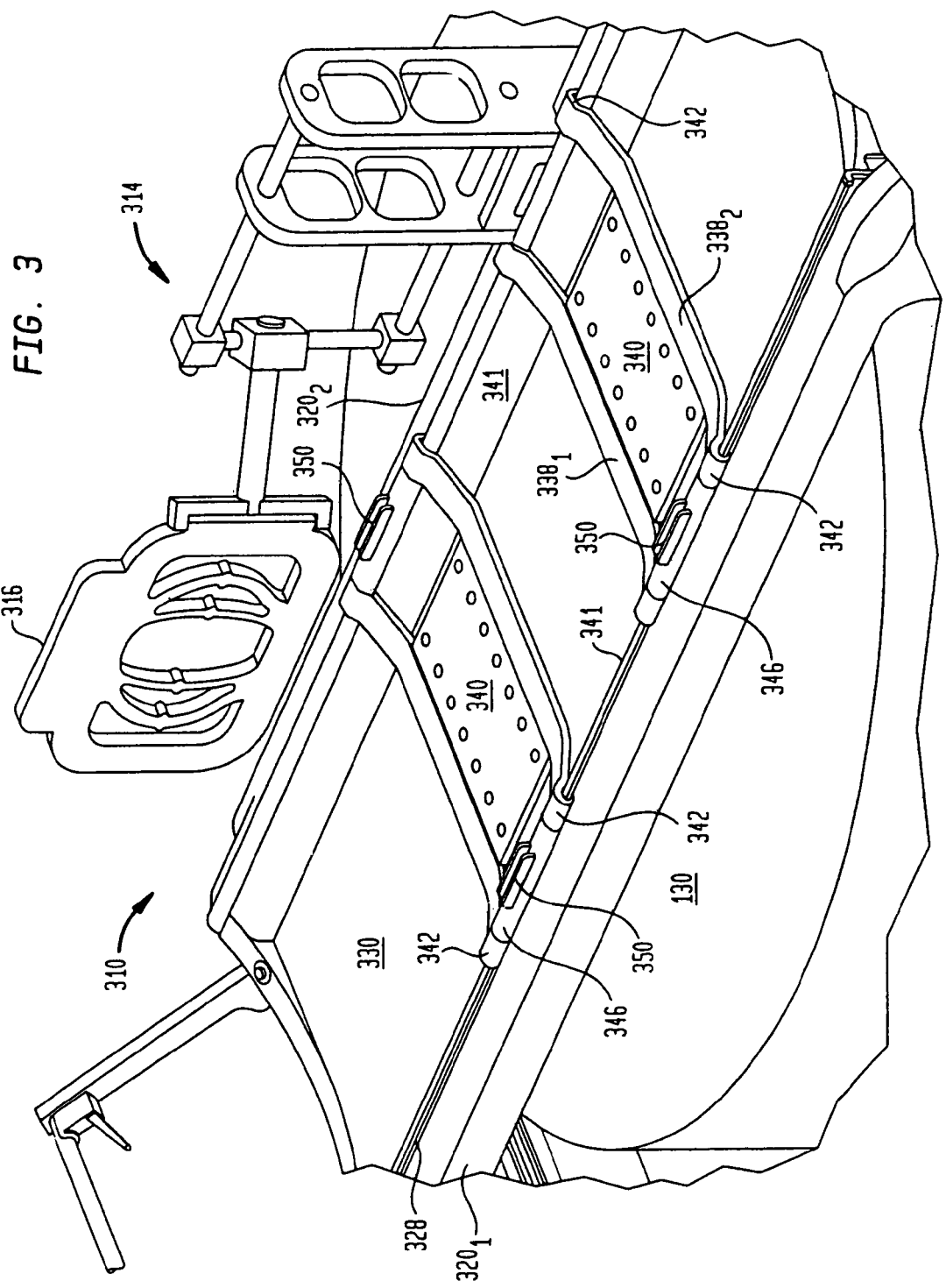
FIG. 3 is perspective view of a magnetic resonance imaging system in accordance with an aspect of the present invention.

Turning now to FIG. 3 there is shown a partial perspective view of a system for performing magnetic resonance imaging assisted surgery. The system comprises a bed 310, an antenna support assembly 314 and an antenna 316. The bed 310 includes a frame 320 and a slab 324 mounted to the frame 320. As shown, the bed 310 is mounted to the lower pole 130 via the frame 320 and is operable to rotate, slide and cantilever as discussed above. The slab 324 includes a pair of longitudinal edges 328 that are spaced apart to define a support surface 330 for a patient. The longitudinal edges 328 are L-shaped in cross-section (see A) and extend slightly above and over frames 320. In this way, the longitudinal edges 328 allow a base member 332 (see FIG. 4) to be slid over the edges 328 as shown.

The base member 332 includes first and second bars 338 that extend parallel to each other and are held apart by a rectangular plate 340 to which they are connected to. The bars 338 are curved towards their ends so they extend up and over the sides 341 of the slab 324. The ends of bars 338 are curved to form hooks 342 that are adapted to engage the longitudinal edges 328 of the slab 324. Support sections 346 are positioned between respective ends of the bars and provide additional connection points for the bars 338.

Figure 4:
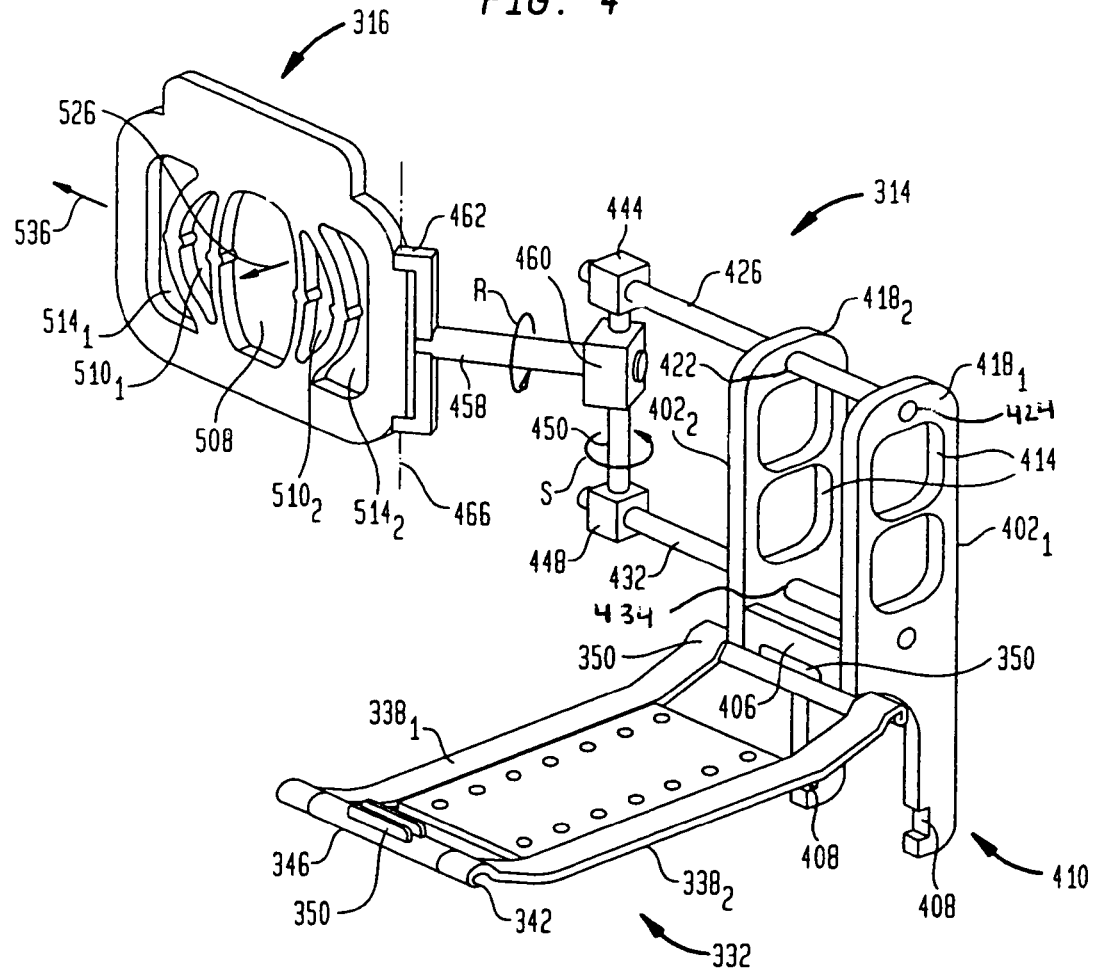
FIG. 4 is a perspective view of an antenna support assembly in accordance with an aspect of the present invention.

Although the sections 346 are not curved in the preferred embodiment to grip the edges 328, they may be curved to hook over the edges 328 of the slab 324. The support sections 346 each include a portion 350 that projects upwardly when the base member 332 is attached to the bed 310. The projecting portions 350 are a position lock for support sections 346. By depress a cam lever to hold it in place, either side holds. By releasing the cam lever the assembly may be slid longitudinally along the bed 310. The types of positional locks are equally well suited. As best seen in FIG. 4, the antenna support assembly 314 includes a pair of sidewalls 402 that are connected together via a cross-sectional beam 406. The beam 406 is shaped at its lower end to engage the rectangular portion 350 of the base member 332. The sidewalls include notches 408 at one end 410. The notches 408 are adapted to engage the frame 320 along its edge proximate the pole 130 and hold the antenna support assembly in place. In the preferred embodiment, the support assembly 314 includes openings 414 towards its distal end 418.

At the distal end 418, openings 422, 424 are formed in each sidewall 402 to receive an upper rod 426. The opening 422 extends completely through the second sidewall $418_2$, while the opening 424 preferably extends into but not through first side wall $418_1$. A lower rod 432 is also arranged parallel to the upper rod 426 through an opening 434 in second sidewall $418_2$. The end of lower rod 432 is inserted into the first sidewall 418, as shown. The other ends of upper and lower rods 426, 432 are inserted into upper and lower rectangular blocks 444, 448. The upper and lower rectangular blocks 444, 448 are connected together by a rod 450 that extends vertically when the antenna support assembly 314 is assembled and attached to the bed 310.

A rod 458 is connected to rod 450 via connecting block 460. The connecting block 460 preferably includes a locking mechanism (e.g., a knob) that when released allows the block 460 and rod 458 to rotate around the rod 450 (see S). A U-shaped holder 462 is formed at the other end of rod 458 and used to hold the antenna 316 in place. In a preferred embodiment the antenna 316 may be connected to holder 462 such that it can be rotated about an axis 466 that runs between the short sections of the holder 462 as shown. Where rotation is employed a locking mechanism to hold the antenna in place during a surgical procedure will also be necessary.

In addition to the types of rotation discussed above, the rod 458 may also be allowed to rotate in the direction R as shown. This would allow the antenna 316 to be rotated between the substantially vertically position shown in FIG. 4 to a position where the antenna 316 is oriented in a substantially horizontal position or any position therebetween. Allowing for the rotation R provides additional versatility to the system. In particular, in some surgical procedures a patient may be required to lie on their side. In such a procedure the antenna 316 can be oriented as shown, i.e., with its planar surfaces extend in a substantially vertical direction. Where a patient is lying on their stomach or back the antenna may then rotated along direction R and parallel to either their back (posterior surface) or stomach (anterior surface). As is discussed in further detail below, this allows for additional flexibility during a surgical procedure.

Turning now to FIG. 5A, there is shown a plan view of the antenna 316 with one side of the housing 504 removed to reveal the internal arrangement of the coils. In accordance with an aspect of the present invention, the housing 504 is formed to provide a skeletal structure that is contoured to match the coil geometry. This results in the housing 504 having openings 508 through which a surgeon, for example, may insert his or her hands during a surgical procedure. As shown in FIGS. 4 and 5, there is a main opening $508_1$ located at the center of the housing, a second pair of openings $508_2$ located on opposite sides of opening $508_1$ and a third pair of openings $508_3$ located next to each of the openings $508_2$. The openings also server to reduce the weight of the antenna 316.

As best seen in FIG. 5A, the housing includes two coils. One coil is a loop coil 524 with a coil vector 526 (see FIG. 4) that is perpendicular to the surface of the housing 504. The second coil 530 includes two runs 530₁ and $530_2$ and includes a coil vector 536 that extends perpendicular to coil vector 526 along the surface of the housing 504, as is shown in FIG. 4. In that regard, the coils 524 and 530 comprise a quad planar coil geometry. Note, however, where a quad planar geometry such as shown in FIG. 5a is employed, rotation along direction R as discussed above may not be desirable as it could result in the coil vector 526 being parallel to direction of the static magnet field, i.e., vertical. The use of the quad planar coil arrangement of FIG. 5 advantageously allows for a larger field of view and deeper penetration into the anatomical area of interest.

Figure 5B:
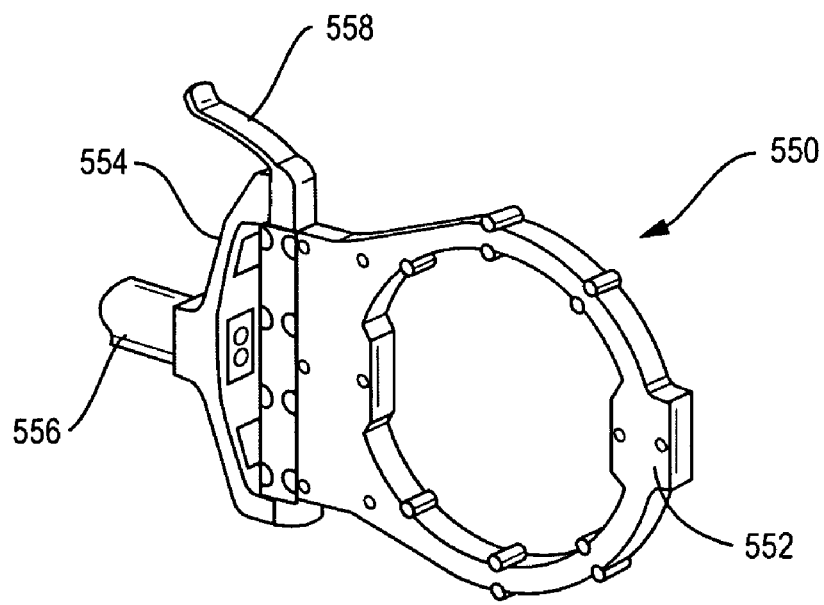
FIG. 5B shows a housing of a planar ring coil assembly.

Referring to FIG. 5B a planar ring coil assembly can be seen. The planar ring coil assembly 550 has a housing 552 which contains a ring coil with a coil vector perpendicular to the surface of the housing 552. The ring coil assembly 550 is shown coupled to a U-Shaped holder 554 which is attached to rod 556. Release lever 558 enables the ring coil assembly 550 to be positioned and then locked into position. The ring coil assembly 550 may be used alternatively to antenna 316 shown in FIG. 4.

Figure 5C:
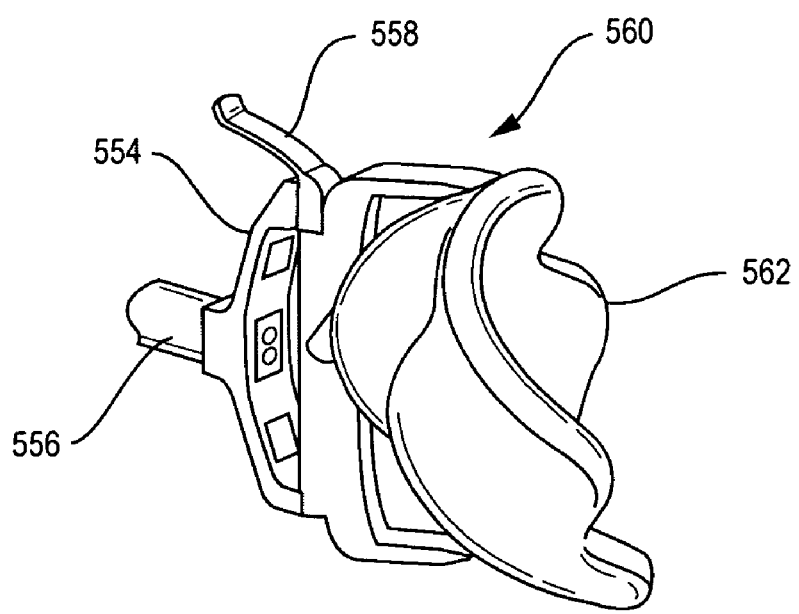
FIG. 5C shows a housing of a double-planar shoulder coil assembly.

FIG. 5C shows a housing of a double-planar shoulder coil assembly. The double-planar shoulder coil assembly 560 has a housing 562 which contains dual coils. The double-planar shoulder coil assembly 550 is shown coupled to a U-Shaped holder 554 which is attached to rod 556. Release lever 558 enables the double-planar shoulder coil assembly 550 to be positioned and then locked into position. The double-planar shoulder assembly 560 may be used alternatively to antenna 316 shown in FIG. 4.

Although the present invention is well suited for use with a planar quad coil and is so described herein, it is equally well suited for use with a planar ring coil and shoulder coil assembly such as a double-planar shoulder coil which are shown as well as with a other MRI coils such as a head coil, spine coil, knee/extremity coil, wrist coil, Planar Thoracic-Lumbar Coil, Quadrature Thoracic-Lumbar Coil, etc.

More particularly, where the coil is oriented as shown in FIG. 3, a patient may lay on their side with coil brought adjacent to their posterior surface, e.g., back. Imaging may then be performed. As the housing includes the openings 508, a surgeon may perform a surgical procedure on the patient's back with the antenna in place. This allows the acquisition of real time images which the doctor may use to locate the surgical site via visual feedback provided by a monitor showing the images. This would allow truly MRI assisted surgery. The placement of a quad planar coil adjacent to patient's anatomy also allows images to be obtained at a greater depth.

Figure 6A:
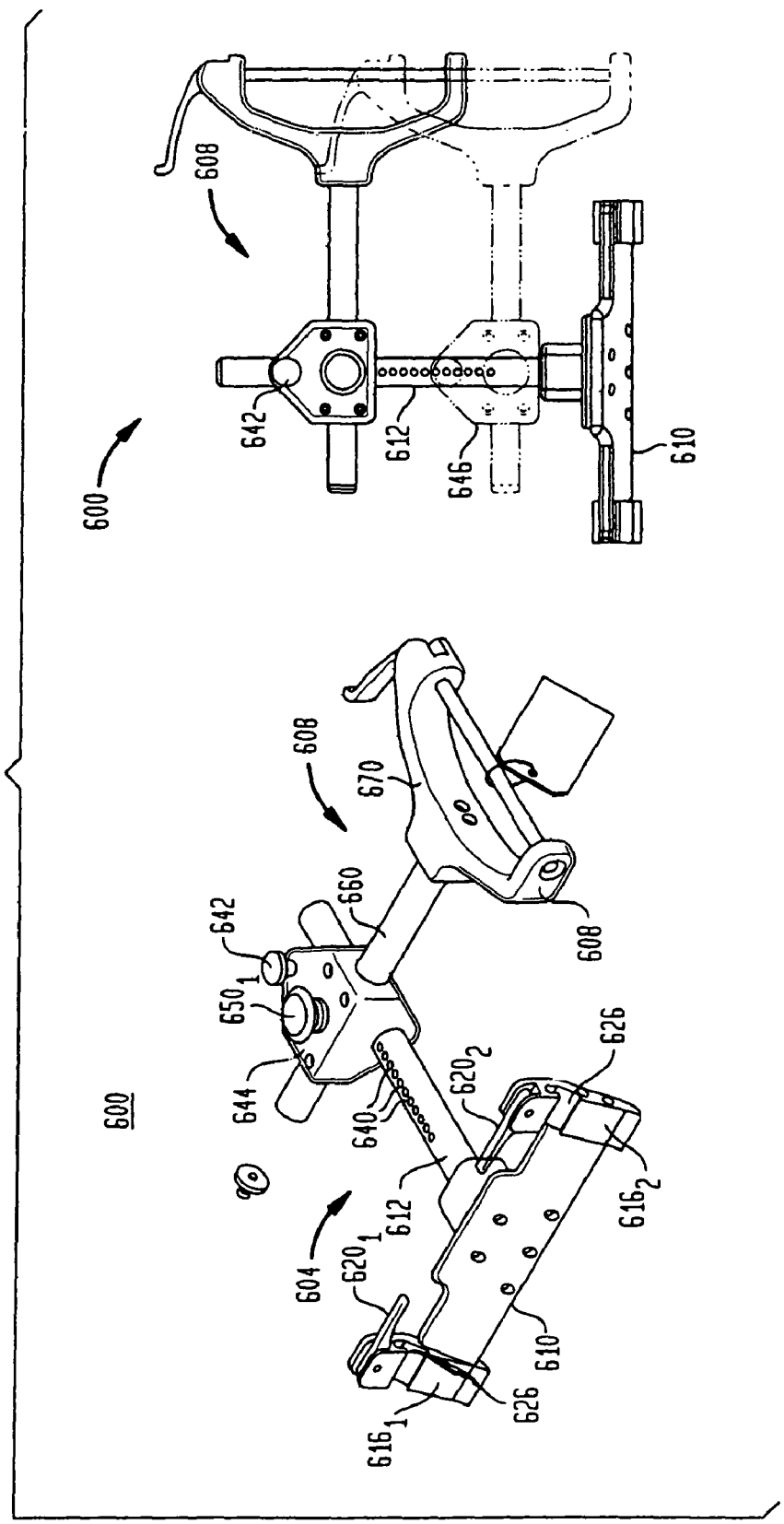
FIG. 6A shows several views of an antenna support assembly in accordance with an aspect of the present invention.

Turning now to FIG. 6A, there is shown an antenna support assembly 600 in accordance with an additional aspect of the present invention. The support assembly 600 may be used in lieu of the assembly 314 discussed above.

The assembly 600 includes a bed locking sub-assembly 604 and coil locking sub-assembly 608. The bed locking sub-assembly 604 includes a base section 610. The base 610 includes end pieces 616 that are affixed to each end. End pieces 616 attaches or locks onto the bed 314 along the longitudinal edges (see FIGS. 7A and 7B) and a rod 612 connected perpendicularly to the base 610. As best seen in the exploded view of FIG. 6B, the end pieces are preferably affixed to the ends of the base using one or more screws 618, although other methods of connecting the ends thereto are also possible. Each end piece includes a locking lever section 622 that is rotatably mounted to the end piece using a spacer 624. The end piece 616 is shaped so as to include a notch or hook section 626. The hook section 626 is adapted to engage the L shaped section A (see FIGS. 3 and 7) of the bed slab and locked into place using the locking levers 622.

Figure 6B:
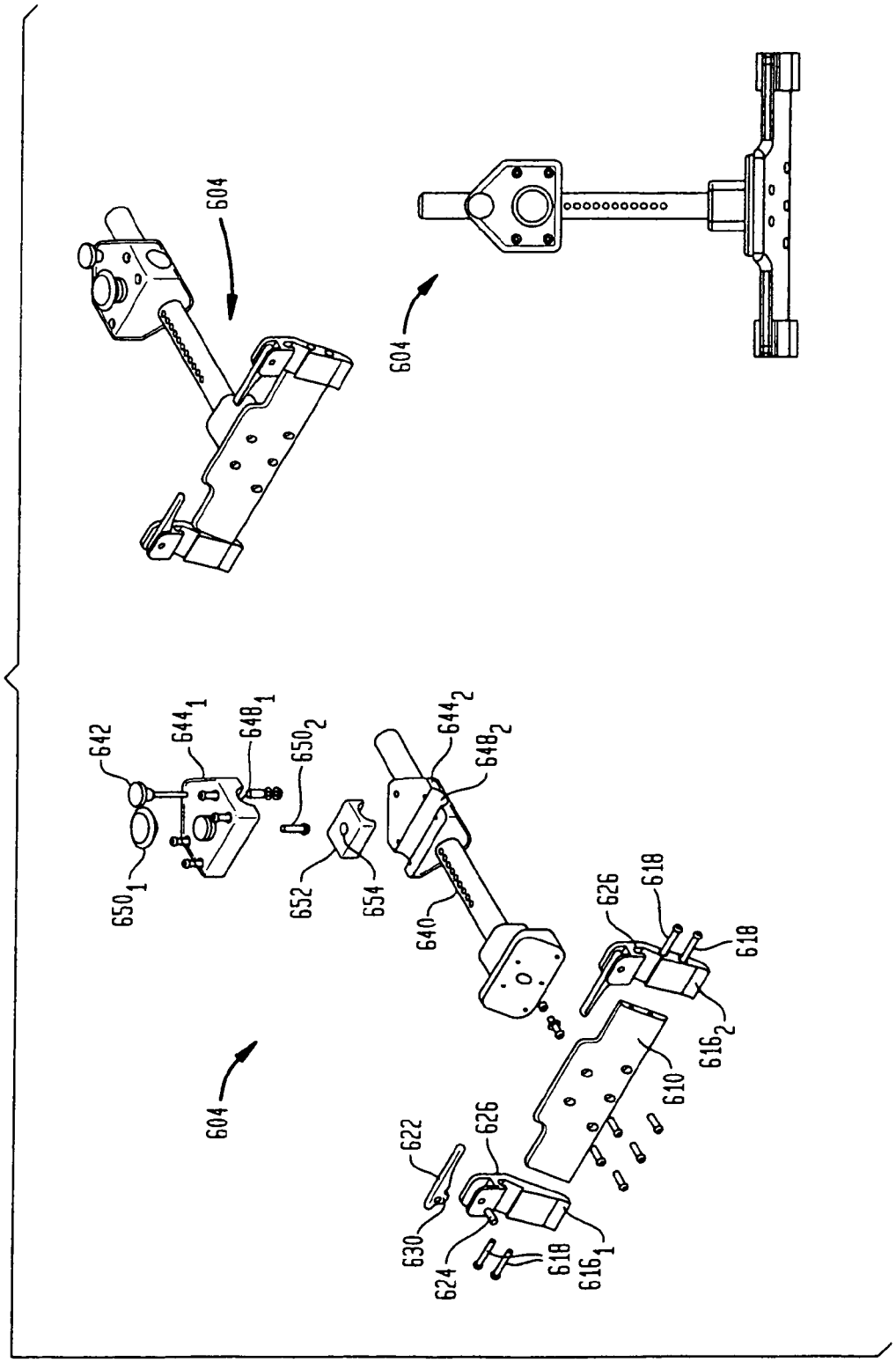
FIG. 6B shows several views of a bed locking sub-assembly in accordance with an aspect of the present invention.
Figure 7A:
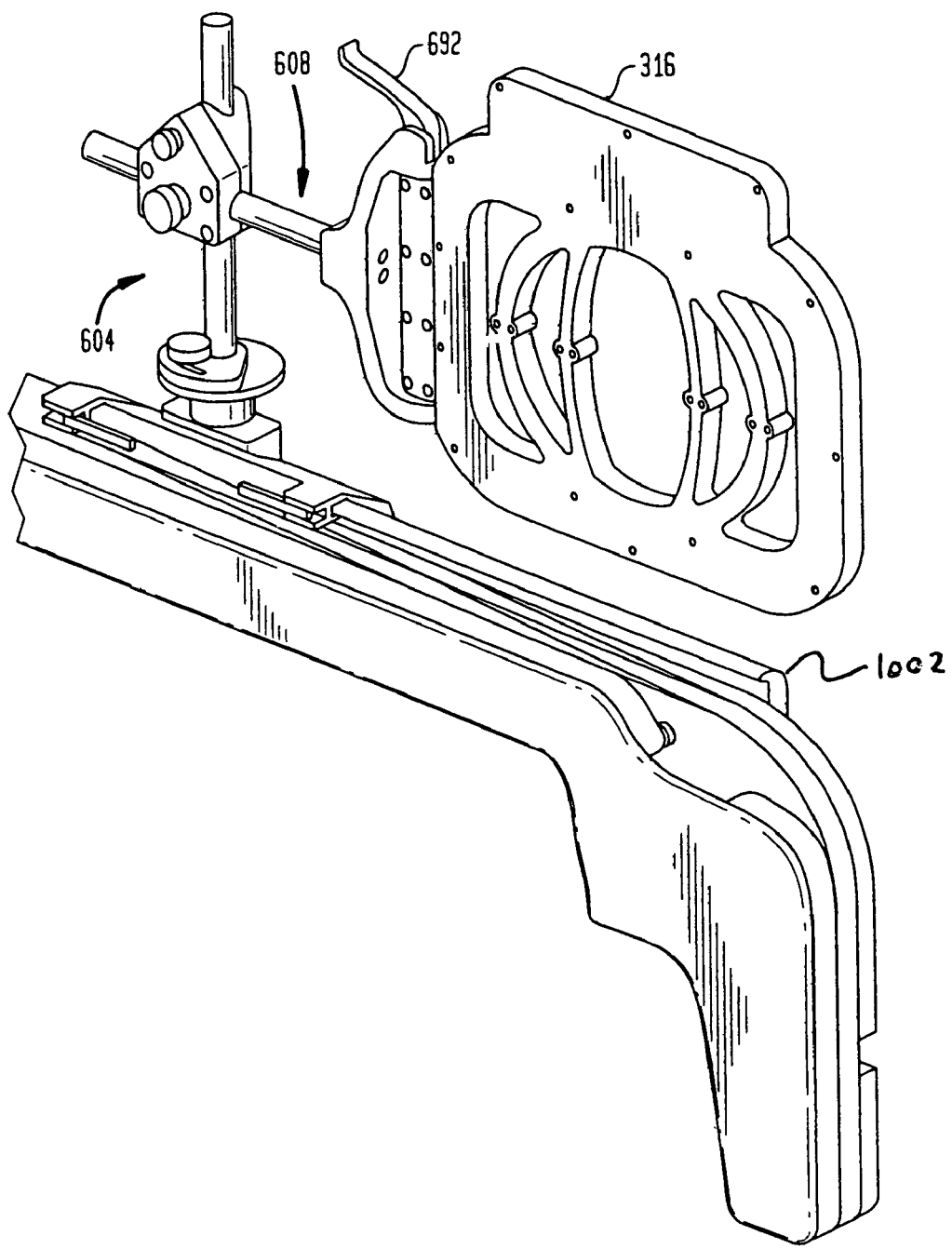
FIGS. 7A and 7B show respective front and rear views of an antenna and bed assembly in accordance with an aspect of the present invention.
Figure 7B:
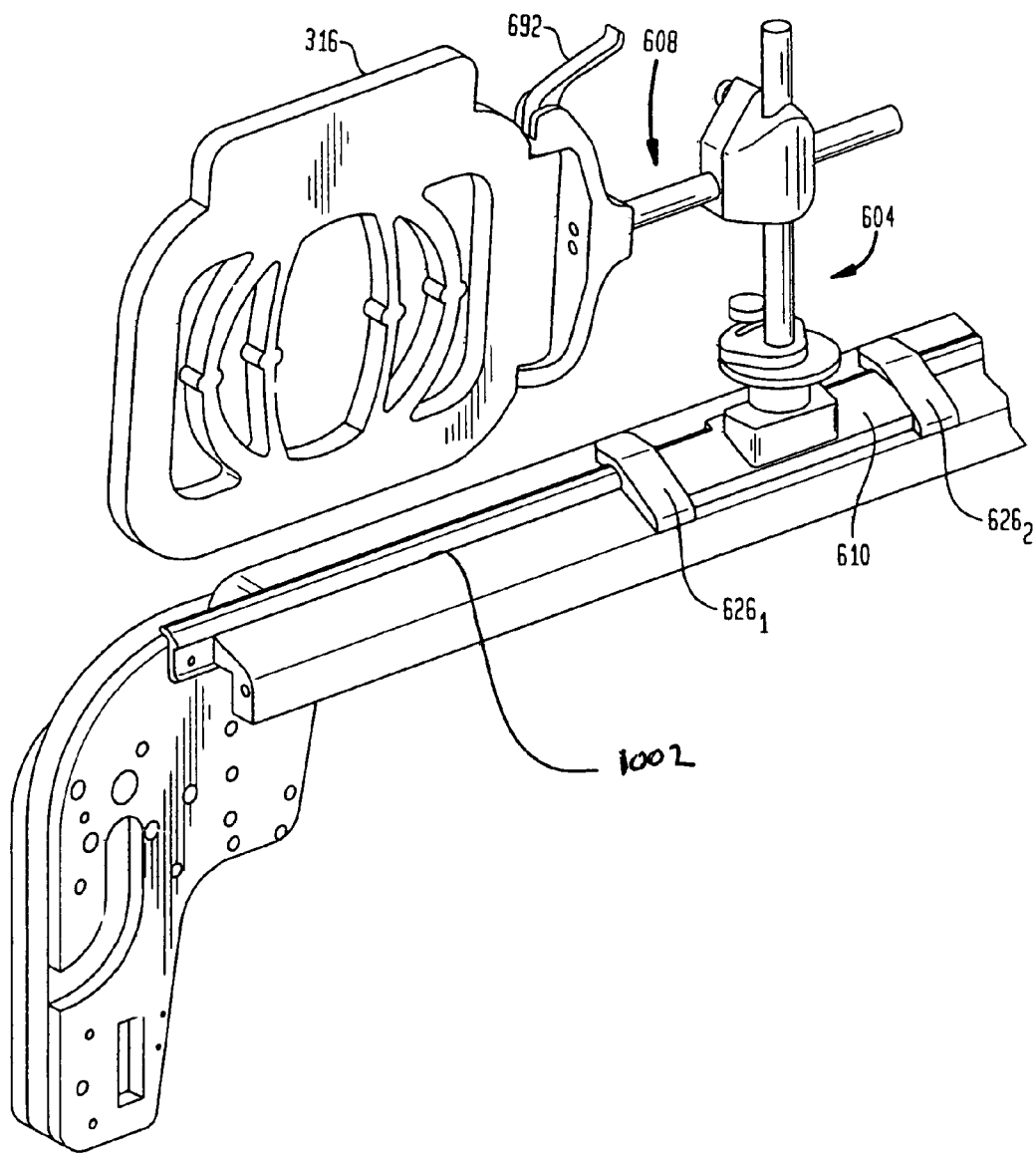

More particularly, with reference to FIGS. 6B and 7A or 7B, the locking levers 622 each include a protruding portion 630. When the levers 622 are rotated upward away from the base section 610, the bed locking assembly 604 may be attached to a longitudinal edge of the slab. Once the hook section 626 is arranged to fit over the edge, the levers are rotated downward toward the base section 610 and the longitudinal edge to which it is attached so that assembly 600 is secured to the bed. When secured, the assembly is oriented as shown in FIG. 7. That is, the base section extends along the edge and such that the rod is oriented in a vertical direction, while coil locking subassembly 608 is oriented in a horizontal direction.

The coil locking sub-assembly 608 is attached to the locking sub-assembly 604 via rod 612. As shown, the rod 612 includes a plurality of openings 640 arranged in a line along its lengthwise direction. These openings 640 are engaged by the knob and pin locking assembly 642. As best seen in FIG. 6B, the locking assembly 642 is inserted through an opening in connection block 644. This locking mechanism 642 allows the position of the connection block 644 to be adjusted along the length of rod 612. When the antenna support assembly is mounted to the bed, this adjustment results in a height adjustment of the coil locking subassembly 608, as is shown in shadow 646 and may be better appreciated from FIG. 7.

The connection block 644 also includes a second locking assembly 650 that allows the coil locking subassembly 608 to be adjusted perpendicular to the direction of the rod 612. As best seen in FIG. 6B, the connection block 644 includes an upper section $644_1$ and a lower section $644_2$. Both sections include a semicircular cut-out 648 as shown. A member 652 is positioned between the upper and lower sections 644. The member 652 includes an opening 654 through which a screw $650_2$ is inserted. The screw $650_2$ extends into the knob $650_1$ and together they form the second locking assembly along with the member 652. As can be appreciated, by adjusting the knob $650_1$, the upper section 644 and member 652 move to allow rod 660 to slid within opening formed by semicircular cut-outs 648. By tightening the knob $650_1$, the rod 660 can be held in place.

The coil locking sub-assembly 608 includes the rod 660 and a holder 670. As best seen in FIG. 6C, the rod 660 is attached to the holder 670 by a pair of screws 672. The holder 670 includes a substantially U-shaped inner side wall 679 having a pair of holes 682 aligned along an axis 684. A cylindrical member 688 is inserted within the holes 682 as shown. The cylindrical member 688 includes a hole running aligned along its axial direction. At one end, a rod 690 is inserted in the hole. In an assembled condition, the rod 690 protrudes from the hole and is inserted through opening 682. The rod 690 serves as a connection point to a lever 692. The lever 692 allows the cylindrical member 688 to be locked in place or released. With the lever 692 in the unlocked position, the cylindrical member 688 is allowed to slide parallel to axis 684 so that an antenna, such as antenna 316, may be positioned within the holder 670 (see FIG. 7). After the antenna is positioned in the holder the member 688 is then slid through hole $682_1$, holes in the antenna, and hole $682_2$ and locked into place using lever 692.

The assembly 600 may be used in a surgical procedure as described above and may be fitted with the quad planar antenna 316 as shown in FIG. 7. In the preferred embodiment the base is approximately 12 inches long and the rod 612 extends approximately 15 inches away from the base 610. The rod 660 of the coil locking assembly 608 is preferably approximately 15 inches long and the distance from the from the end of the lever 692 to the other end of the holder 670 is approximately 11 inches.

Figure 8:
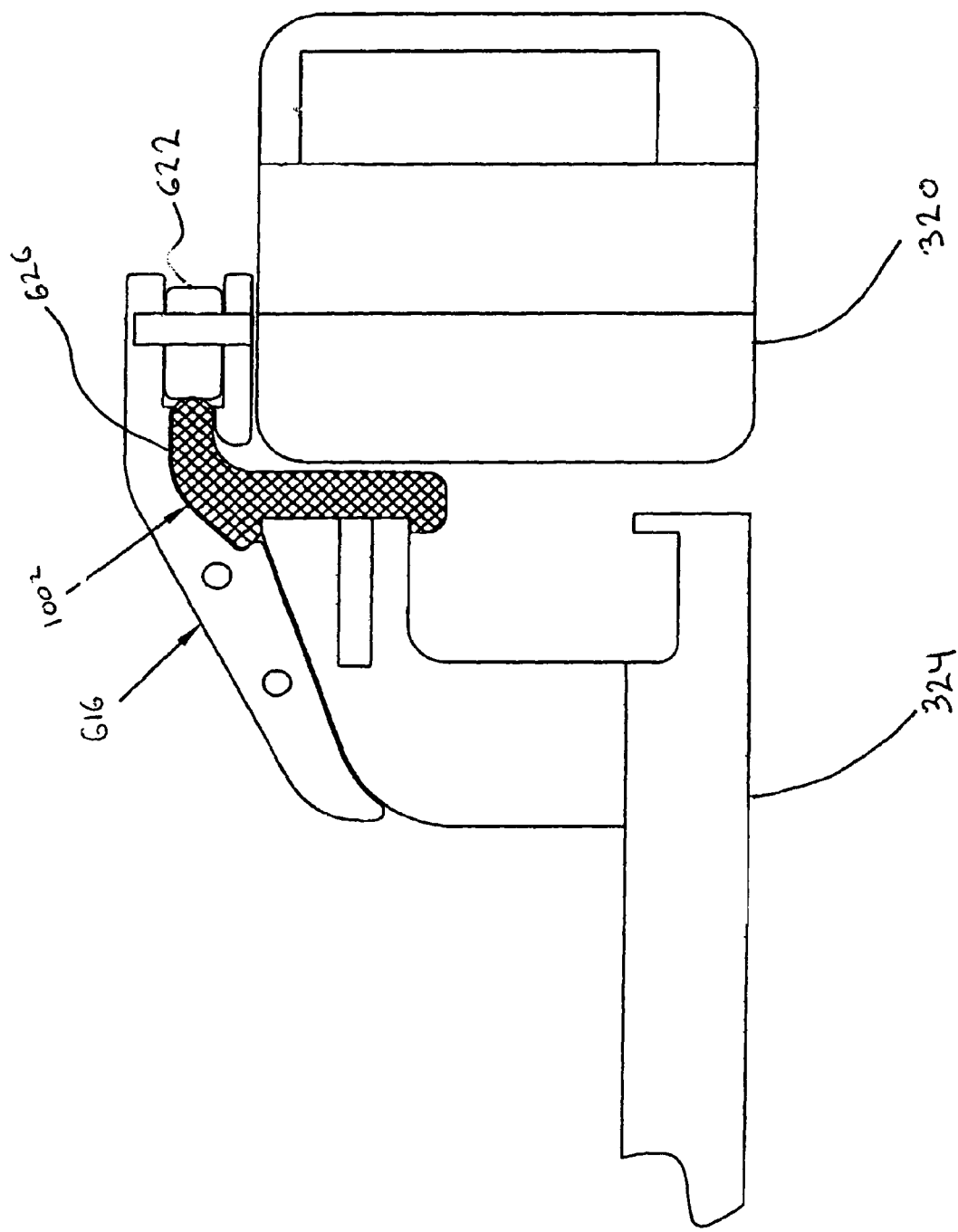
FIG. 8 shows a cross section detail of the bed extrusion.

Referring to FIG. 8 shows a cross section detail of the bed extrusion. End pieces 616 are affixed to each end the base 610 (not shown in this figure). The end pieces 616 attaches or locks onto the bed 314 along the longitudinal edge 1002 (shown in FIGS. 7A and 7B as well). Each end piece 616 includes a locking lever section 622 that is rotatably mounted to the end piece using a spacer. The end piece 616 is shaped so as to include a notch or hook section 626. The hook section 626 is adapted to engage the L shaped section A 1002 of the bed slab and locked into place using the locking levers 622.

The support assembly 600 is simpler in design than assembly 314, includes less parts and attaches to bed without the aid of the base member 332.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for performing a surgical procedure, comprising:
    positioning a patient on bed in a receiving space of a stationary magnetic resonance imaging magnet;
    positioning an antenna coil assembly adjacent to a portion of the patient's anatomy;
    acquiring magnetic resonance image data of the patient's anatomy adjacent the antenna coil assembly;
    performing a surgical procedure on the patient's anatomy adjacent the antenna coil assembly during acquisition of the magnetic resonance image data; and
    repetitively acquiring image data of the patient's anatomy adjacent the antenna coil assembly as the surgical procedure is performed.

2. The method as recited in claim 1 further comprising the step of aligning the antenna coil to the portion of the patient's anatomy.

3. The method as recited in claim 1 further comprising positioning the antenna coil assembly adjacent to the patient's anterior surface.

4. The method as recited in claim 1 further comprising positioning the antenna coil assembly adjacent to the patient's posterior surface.

5. The method as recited in claim 1 further comprising positioning the antenna coil assembly adjacent to the patient's side surface.

6. The method of claim 1, further comprising viewing the acquired magnetic resonance images of the patient's anatomy in real time.

7. The method of claim 1, wherein the surgical procedure is a biopsy.

8. The method of claim 1, further comprising using the acquired magnetic resonance images to pinpoint a location within the patient's body.

9. The method of claim 8, wherein the pinpointed location is that of a tumor, tissue, bones, or organs.

\* \* \* \* \*

UNITED STATES PATENT AND TRADEMARK OFFICE
CERTIFICATE OF CORRECTION

| | |
|---|---|
| PATENT NO. | : 7,999,547 B2 |
| APPLICATION NO. | : 12/381718 |
| DATED | : August 16, 2011 |
| INVENTOR(S) | : Charles A. Green, Arto Cinoglu and William H. Wahl |

It is certified that error appears in the above-identified patent and that said Letters Patent is hereby corrected as shown below:

On the Title Page, Item (75), under Inventors:, "Oceanside" should read --Rockville Centre--.

Signed and Sealed this
Fourteenth Day of August, 2012

David J. Kappos
*Director of the United States Patent and Trademark Office*